(12) United States Patent
Kudlicki et al.

(10) Patent No.: US 6,448,033 B1
(45) Date of Patent: Sep. 10, 2002

(54) METHOD OF SYNTHESIZING A FLUORESCENTLY LABELED PROTEIN

(75) Inventors: Wieslaw Kudlicki; Gisela Kramer; Boyd Hardesty, all of Austin, TX (US)

(73) Assignee: Research Development Foundation, Carson City, NV (US)

( * ) Notice: Subject to any disclaimer, the term of this patent is extended or adjusted under 35 U.S.C. 154(b) by 1577 days.

(21) Appl. No.: 08/590,729

(22) Filed: Jan. 24, 1996

Related U.S. Application Data (63) Continuation of application No. 08/333,733, filed on Nov. 3, 1994, now abandoned.

(51) Int. Cl.[7] .............................. C12P 21/06; C12Q 1/68
(52) U.S. Cl. ........................ 435/69.1; 435/68.1; 435/6
(58) Field of Search .............................. 435/69.1, 68.1, 435/6

(56) References Cited

U.S. PATENT DOCUMENTS 5,258,862 A * 11/1993 Hardesty et al. ......... 435/172.3

OTHER PUBLICATIONS

Kudlicki, W. et al. (1992) "High efficiency cell–free synthesis of proteins: Refinement of the coupled transcription/translation system" *Anal. Biochem.* 206:389–393.*

Picking, W.D. et al. (1992) "Fluorescence characterization of the environment encountered by nascent polyalanine and polyserine as they exit *Escherichia coli* ribosomes during translation" *Biochem.* 31:2368–2375.*

Hildenbrand, K. et al. (1982) "Sugar transport by the bacterial phosphotransferase system" *J. Biol. Chem.* 257(23):14518–14525.*

Stryer, L. (1988) *Biochemistry*. W.H. Freeman and Company, New York. pp. 752–758.*

* cited by examiner

*Primary Examiner*—Ponnathapu Achutamurthy
*Assistant Examiner*—Richard Hutson
(74) *Attorney, Agent, or Firm*—Benjamin Aaron Adler (57) ABSTRACT

The present invention provides a method of synthesizing a fluorescently labeled protein in a cell free protein synthesis system, comprising the steps of: (a) incubating a sample of ribosomes obtained from a cell-free extract with plasmid DNA containing a coding sequence for a protein of interest, said sample incubated in a coupled transcription/translation medium together with a aminoacyl tRNA having fluorescent label; (b) partially purifying said fluorescently labeled protein by separating newly synthesized, fluorescently-labeled protein from other fluorescent components within said sample; (c) measuring the amount of protein synthesized; (d) determining fluorescence of newly synthesized protein; and (e) determining the biological activity of the newly synthesized protein.

3 Claims, 5 Drawing Sheets

METHOD OF SYNTHESIZING A FLUORESCENTLY LABELED PROTEIN

This is a continuation of application Ser. No. 08/333,733 filed on Nov. 3, 1994, now abandoned.

BACKGROUND OF THE INVENTION

1. Field of the Invention

The present invention relates generally to the fields of molecular biology, biotechnology and protein synthesis. More specifically, the present invention relates to a novel method of synthesizing a fluorescently labeled protein in a cell-free protein synthesis system.

2. Description of the Related Art

Several lines of evidence indicate that nascent polypeptides acquire secondary and tertiary structure on ribosomes. Beckmann and his coworkers (1990) provided evidence that Hsp70 interacts with nascent proteins and postulated cotranslational folding. The ribosome itself may play an important role in the folding process. Lim and Spirin (1986) hypothesized that a nascent peptide must be synthesized as an α helix. The use of fluorescence techniques to study extension and folding of nascent peptides and proteins on ribosomes has been reviewed. Previously, these techniques were applied to demonstrate nascent MS2 protein folds while bound to ribosomes. Chaperones have been shown to facilitate folding of many proteins from their denatured state, but very little is known of whether these proteins function on ribosomes during translation. Hartl and coworkers presented data indicating that DnaJ is the first chaperone that binds to the nascent peptides of firefly luciferase or chloramphenicol acetyl transferase on wheat germ ribosomes (Hendrick et al., 1993).

The prior art is deficient in the lack of effective means synthesizing a fluorescently labeled protein in a cell-free protein synthesis system. The present invention fulfills this longstanding need and desire in the art.

SUMMARY OF THE INVENTION

In the present invention, coumarin from coumarin-maleimidyl-SAcMet-tRNA$_f$ (CPM-SAcMet-tRNA$_f$) was incorporated into the N-terminus of nascent polypeptides that were synthesized on ribosomes in a bacterial cell-free coupled transcription/translation system. Fluorescence techniques were used to monitor changes in the local environment and mobility of the N-terminal probe and in turn effects of the chaperones on folding, activation and release of the nascent or full-length polypeptides from the ribosomes. The present invention shows that the chaperones affect folding of nascent rhodanese polypeptides while these are bound as peptidyl-tRNA on ribosomes. The chaperones facilitate their release from the ribosomes as enzymatically active protein.

In one embodiment of the present invention, there is provided a method of synthesizing a fluorescently labeled protein in a cell-free protein synthesis system, comprising the steps of: (a) incubating a sample of ribosomes obtained from a cell-free extract with plasmid DNA containing a coding sequence for a protein of interest, said sample incubated in a coupled transcription/translation medium together with an aminoacyl tRNA having fluorescent label; (b) partially purifying said fluorescently labeled protein by separating newly synthesized, fluorescently-labeled protein from other fluorescent components within said sample; (c) measuring the amount of protein synthesized; (d) determining fluorescence of newly synthesized protein and (e) determining the biological activity of the newly synthesized protein.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows the quenching of coumarin fluorescence by nitromethane. Stern-Volmer plots of steady state fluorescence intensity are given for CPM-rhodanese released or bound to ribosomes in comparison to free CPM-SAc-Met-tRNA (line 1) and this tRNA bound to ribosomes (line 6). Line 2, CPM-rhodanese in the supernatant in enzymatically active form; line 3, CPM-rhodanese released with DnaK; line 4, CPM-rhodanese released with puromycin; line 5, CPM-rhodanese bound to ribosomes.

FIG. 4 shows the DnaJ affects the interaction of anti-coumarin IgG with ribosome-bound CPM-rhodanese. First, the spectrum of CPM-rhodanese on ribosomes after incubation with sparsomycin was taken (solid line). Three parallel samples were set up (CPM-rhodanese on ribosomes incubated with sparsomycin) to which were added DnaJ or DnaK alone or both together. Spectra were taken (not shown) and analyzed. The data were found to be identical or very similar to those given in Table VI. Then each sample received anti-coumarin IgG. After an incubation of 10 minutes at room temperature, the spectra were taken and are shown here. (x—x) DnaJ+IgG; (•••) DnaK+IgG; (—-)DnaJ and DnaK+IgG.

DETAILED DESCRIPTION OF THE INVENTION

In describing the present invention, the following abbreviations are used: RHO, rhodanese; CPM, 3-(4- maleimidophenyl)-4-methyl-7-(diethylamino) coumarin; CPM-rhodanese, rhodanese labeled at its N-terminal methionine with CPM; SDS-PAGE, sodium dodecyl sulfate-polyacrylamide gel electrophoresis; anti-CPM IgG, anti-coumarin rabbit polyclonal antibodies; CPM-SAc-Met-tRNA$_f$, initiator tRNA which has been aminoacylated with methionine and then labeled on the methionine amino group via mercaptoacetic acid by CPM; IgG, immunoglobulin; Fab, its papain-generated fragment.

The present invention is also directed to a method of synthesizing a fluorescently labeled protein in a cell-free protein synthesis system, comprising the steps of: (a) incubating a sample of ribosomes obtained from a cell-free extract with plasmid DNA containing a coding sequence for a protein of interest, said sample incubated in a coupled transcription/translation medium together with a aminoacyl tRNA having fluorescent label; (b) partially purifying said fluorescently labeled protein by separating newly synthesized, fluorescently-labeled protein from other fluorescent components within said sample; (c) measuring the amount of protein synthesized; (d) determining fluorescence of newly synthesized protein and (e) determining the biological activity of the newly synthesized protein.

Generally, in the present invention, the flurorescent label is on the N-terminus of said protein. In a preferred embodiment, the aminoacyl tRNA used in the present method is an methionyl-tRNA-$^{Methinine/f}$. Preferably, the flurorescent label is covalently attached to the amino acid of an initiator tRNA.

In the method of the present invention, the transcription/translation medium will normally contain RNA polymerase, nucleoside triphosphates, an energy regenerating system and amino acids in a buffered salt solution. In a preferred embodiment, the ribosomes are isolated from an *E. coli* extract called S30. In a preferred embodiment, the plasmid DNA is non-linearized. Preferably, the incubation of step (a) is for about 30 minutes at about 37° C. Also, in the method of the present invention, the fluorescently labeled protein is partially purified by a method selected from the group consisting of centrifugation, ionic exchange chromatography and gel filtration.

The following examples are given for the purpose of illustrating various embodiments of the invention and are not meant to limit the present invention in any fashion.

EXAMPLE 1

Chemicals

Nucleoside triphosphates and *E. coli* tRNA were purchased from Boehringer-Mannheim; 3-(4-maleimidophenyl)-7-diethylamino-4-methylcoumarin (CPM) was from Molecular Probes Inc. (Eugene, Oreg.). tRNA$^{Met}_f$, rifampicin, puromycin, sparsomycin and all other biochemicals were from Sigma. A mixture of ribonuclease A and TI ("RNase Cocktail") was from Ambion (Austin, Tex.). [$^{14}$C]Leucine and [$^{35}$S]methionine were purchased from NEN-Dupont. The chaperones DnaK, DnaJ, GrpE, GroEL and GroES were bought from Epicentre Technologies (Madison, Wis.). The original rhodanese plasmid, rhodanese isolated from bovine liver mitochondria and polyclonal anti-rhodanese antibodies were from Dr. Paul Horowitz (University of Texas Health Science Center, San Antonio, Tex.). Polyclonal antibodies against *E. coli* release factors 1 and 2 were provided by Dr. Warren Tate (University of Otago, New Zealand). Second antibodies (goat-anti-rabbit IgG-horse radish peroxidase and rabbit-anti-sheep IgG horse radish peroxidase) were purchased from Zymed (South San Francisco, Calif.)

EXAMPLE 2

In vitro Systems

Propagation of the plasmid, isolation of SP6 RNA polymerase and preparation of the *E. coli* cell-free extract (S30) as well as the isolation of the ribosome fraction from the S30 were carried out as described by Kudlicki et al., *Anal. Biochem.* 206:389 (1992). Basically, plasmid preparations were made by standard procedures (J. Sambrook et al. (1989) *Molecular Cloning*, Cold Spring Harbor Laboratory Press) except that the CsCl centrifugation step was replaced by Q cartridge (Bio-Rad) chromatography. SP6 and T7 RNA polymerases are commercially available. The ribosome fraction used was isolated from the S30 fraction prepared according to G. Zubay from *E. coli* K12 (A19). Cells were grown at 37° C. in LB (Sigma) broth to which 20% glucose (10 ml per 2 liter medium) was added. Cells were harvested in mid-log phase at 37° C. and lysed in a pressure cell. The cells were then centrifuged for 30 minutes at 30,000×g and the S30 extract was prepared. A protease inhibitor, phenyl-methylsulfonyl fluoride, was added to the lysis buffer to give a final concentration of 0.5 mM. Aliquots of the S30 (9 ml each) were centrifuged at 47,000 rpm for 4 hours in a Beckman Ti 50 rotor. The sedimented ribosomes were resuspended in 1.0 ml of 20 mM Tris-HCl (pH 7.5), 10 mM Mg(OAc)$_2$, and 1 mM DTT resulting in a suspension of about 1200 A$_{260}$ units/ml. This ribosome fraction was stored at −70° C. in small aliquots.

The preparation of CPM-SAcMet-tRNA$_f$ was as described previously for labeling of the α-amino group of Phe-tRNA$^{Phe}$ with CPM (Odom et al., 1990). Briefly, the α-amino group of methionine in [$^{35}$S]Met-tRNA$_f$ was acylated with dithiodiglycolic acid and then reduced to the corresponding thioglycolic acid derivative. Its sulfhydryl group was reacted with the maleimide (CPM). Anti-CPM antibodies were raised in rabbits; the IgG fraction from the serum of the immunized rabbit was prepared as described (Picking et al., 1992).

The in vitro system for coupled transcription/translation has been detailed (Kudlicki et al., 1992). Briefly, the system used to carry out coupled transcription/translation contained in a total volume of 30 μl: 50 mM Tris-acetate (pH 7.8), 14 mM Mg(OAc)$_2$, 36 mM NH$_4$OAc, 72 mM KOAc, 2 mM Ca(OAc)$_2$, 0.5 mM EDTA, 2% polyethylene glycol-6000, 2 mM DTT, 1.2 mM ATP, 0.8 mM each of GTP, UTP, and CTP, 0.5 mM cAMP, 27 mM phosphoenol pyruvate, 0.35 μg pyruvate kinase, 1 μg folinic acid, 83 μM $^{14}$C-leucine, 330 μM of each of the other 19 amino acids, 20 μg *E. coli* tRNA (Boehringer), 0.5 μg rifampicin, 0.3 mM glucose-6-phosphate, 1.2 A$_{260}$ units of the *E. coli* ribosome fraction, 0.5 μg plasmid DNA, and 0.5 μg SP6 RNA polymerase. $^{14}$C-leucine was diluted to 40 Ci/mole for the assay. Incubation was for 30 minutes at 37° C. For the large scale synthesis of CPM-rhodanese, the reaction mixtures were enlarged to 0.9 ml and contained the salts and low molecular weight components listed above plus 5 mM Na$_2$S$_2$O$_3$. About 60 A$_{260}$ units of unwashed ribosomes were incubated with about 10–15 μg non-linearized plasmid (pSP65) containing the rhodanese coding sequence under the SP6 promoter. CPM-SAc[$^{35}$S]Met-tRNA$_f$ (350 Ci/mol) was used as radioactive precursor; folinic acid was omitted. In some control experiments, [$^{14}$C]leucine (40 Ci/mol) was used together with nonradioactive fMet-tRNA$_f$. After incubation for 30 minutes at 37° C., the sample was loaded over 0.6 ml of buffered sucrose and centrifuged for 45 minutes at 45,000 rpm. Then, the supernatant was collected and saved, the sucrose layer was removed; the ribosomal pellet was rinsed, then resuspended in 60 μl of 20 mM Tris-HCl, pH 7.5, 10 mM Mg(OA)$_2$, 30 mM NH$_4$OAc, 1 mM DTT, 5 mM Na$_2$S$_2$O$_3$ (Solution A). Immediately after centrifugation, the supernatant fraction (about 0.9 ml) was treated with ribonucleases A and T1 (0.1 mg and 2,000 U/ml, respectively) for 15 minutes at 37° C. to degrade remaining CPM-SAc [$^{35}$S]Met-tRNA$_f$. The resulting reaction mixtures was then chromatographed on a Sephadex G100 column (1×20 cm) equilibrated in Solution A to separate newly synthesized CPM-labeled rhodanese from low molecular weight degradation products containing coumarin and [$^{35}$S]methionine.

EXAMPLE 3
Fluorescence Measurements

Fluorescence measurements were carried out on a model 8000C photon-counting spectrofluorometer from SLM-Aminco Instruments Inc. (Urbana, Ill.). Spectra were measured at 1-nm emission intervals at a scanning rate of 0.5 seconds per wavelength increment; the excitation wavelength was 390 nm. Spectra and relative quantum yields were normalized on the basis of radioactivity from [$^{35}$S] methionine that was present as CPM-SAc-methionine in the sample. Relative fluorescence quantum yields were determined from integrated emission spectra. The relative quantum yield of CPM-rhodanese in the supernatant fraction was taken as 1.00 and all other quantum yields are given relative to this value. Fluorescence anisotropy was determined as described in Odom et al. (1984) at an emission wavelength of 480 nm. For the fluorescence studies, an aliquot of the resuspended ribosomes or of the treated supernatant fraction was incubated in the cuvette in a total volume of 420 µl containing salts and low molecular weight components as above for the coupled transcription/translation but without amino acids and without UTP and CTP (Solution B). After the spectrum was taken, the components to be tested were added in a minimum volume. The cuvette was incubated for 10 minutes at 37° C. before the spectrum was taken again. Additions were: anti-CPM-IgG, 0.1 mg; chaperones GroES, 1.6 µg; GroEL, 6 µg; DnaK, 4 µg; DnaJ, 2 µg; GrpE, 3 µg.

EXAMPLE 4
Rhodanese Quantitation

Precipitation of protein by trichloroacetic acid (TCA) to quantitate the amount of rhodanese polypeptides, analysis by SDS-PAGE and autoradiography were carried out as is well known in the art. Rhodanese activity was assayed according to Sorbo (1953) as given in Tsalkova et al. (1993). Basically, enzymatic activity of rhodanese was determined in a calorimetric assay which measures the conversion of CN$^-$ to SCN$^-$ by the enzyme using S$_2$O$_3^{2-}$ as substrate. SCN$^-$ formed was detected and quantitated by measuring absorbance at 460 nm of a complex between this product and ferric ions. One unit is defined as the amount of enzyme generating 1 µmol product/minute at 37° C. in this assay system.

Western blots from SDS-PAGE were probed with bovine antibodies against release factors 1 or 2 or with rabbit anti-rhodanese antibodies, then with the respective second antibody to which horseradish peroxidase had been linked. Peroxidase was detected by chemiluminescence using Amershams's ECL products.

EXAMPLE 5
Folding of Rhodanese Labeled with Coumarin at its N-terminus

Figure 1:
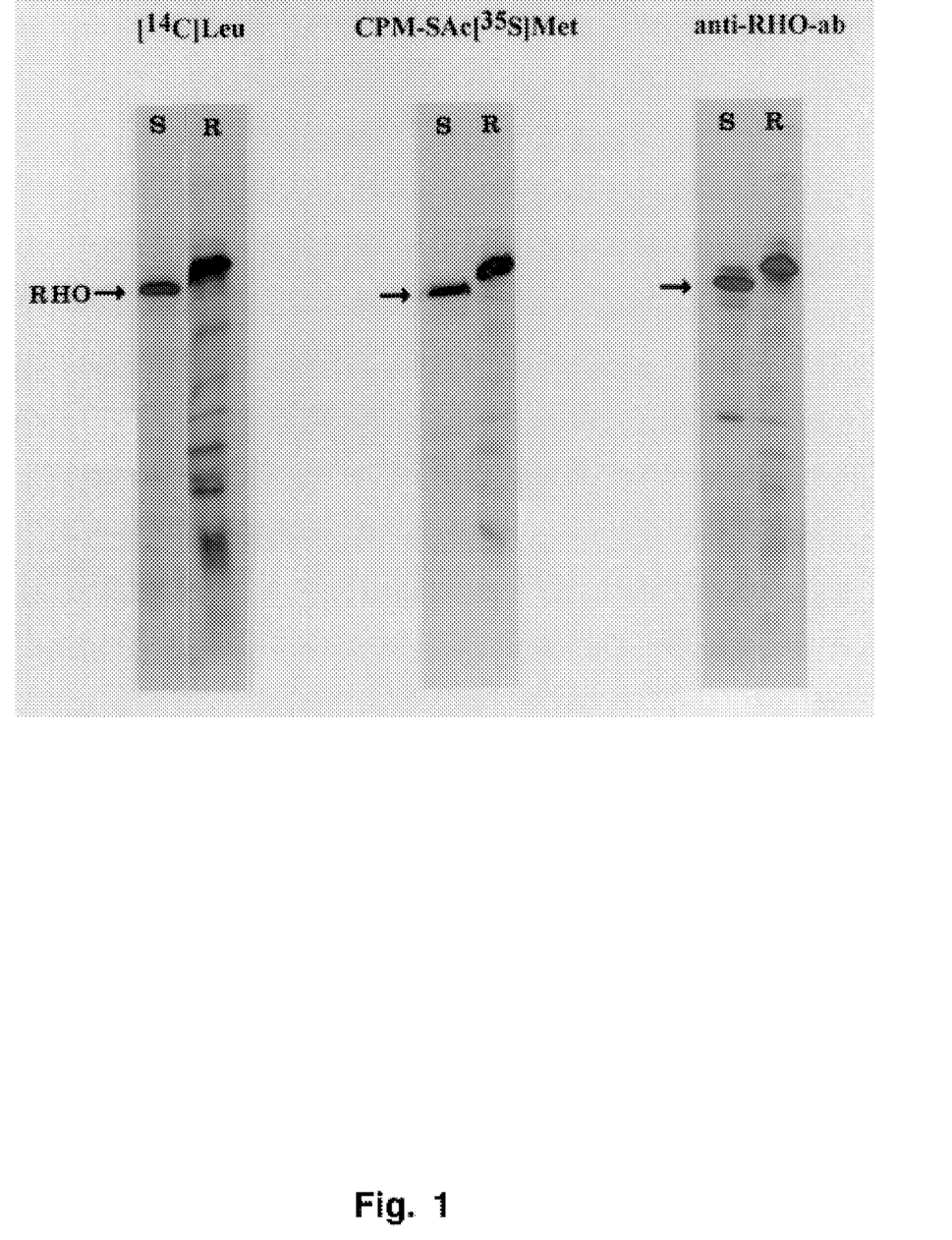
FIG. 1 shows an analysis of free and ribosome-bound rhodanese either translated in the presence of [$^{14}$C]leucine or initiated with CPM-SAc-[$^{35}$S]Met-tRNA$_f$. Rhodanese was synthesized by coupled transcription/translation either with [$^{14}$C]leucine (160 Ci/mol) or with CPM-SAc-[$^{35}$S]Met-tRNA$_f$ (4,000 Ci/mol) as radioactive precursor. After incubation, the reaction mixture was centrifuged. The supernatant and the resuspended ribosomes were analyzed by SDS-PAGE and autoradiography. The autoradiogram is shown (first 2 parts labeled as $^{14}$C-leucine and CPM[$^{35}$S]Met, respectively). Tracks 1 and 2, from incubations with internal [$^{14}$C]leucine; tracks 3 and 4, from incubations with N-terminal CPM-SAc-[$^{35}$S]methionine. Tracks 1 and 3, 20 ul of the supernatant; tracks 2 and 4, 20 ul of the resuspended ribosomes. The third part of FIG. 1 (labeled anti-RHO ab) shows the Western blot probed with anti-rhodanese antibodies. The position of horseradish peroxidase covalently linked to the second antibody was visualized using Amersham's ECL system. The arrow indicates the electrophoretic. mobility of native rhodanese from bovine liver.

To monitor the effects of chaperones during folding and activation of nascent rhodanese, coumarin was translationally incorporated at the N-terminus of the enzyme from CPM-S Ac [$^{35}$S]Met-tRNA$_f$. Met-tRNA$_f$ formed enzymatically was derivatized by chemical reaction, then used to initiate protein synthesis on *E. coli* ribosomes as described above. Incorporation of CPM-SAc [$^{35}$S]methionine at the N-terminus of polypeptides formed in a coupled transcription/translation system was monitored by radioactivity after trichloroacetic acid precipitation of the in vitro synthesized rhodanese polypeptides. The product was identified by SDS-PAGE and autoradiography as shown in FIG. 1. The analysis was carried out after separation of the ribosomes from the supernatant fraction. There is a difference in migration on SDS-polyacrylamide gels of full-length rhodanese in the supernatant and in the ribosome fraction, respectively.

To further identify these full-length forms of the product synthesized during coupled transcription/translation, the polypeptides from the SDS-polyacrylamide gel were transferred to a PVDF-membrane and probed with anti-rhodanese antibodies. FIG. 1 indicates that both full-length forms were recognized by the anti-rhodanese antibodies. Since the ribosome-bound polypeptide can be converted into enzymatically active soluble protein, the present invention shows conclusively that the polypeptide is a precursor form of the soluble enzyme.

The nature of the difference between the soluble and ribosome-bound polypeptide is not known. One possibility is that the slower migrating form is covalently linked to tRNA or a nucleotide fragment derived from it. That this hypothesis is incorrect is indicated by the following observations: the electrophoretic migration pattern is not affected by preincubation of the sample with a cocktail of ribonucleases or by preincubation at pH 10.5 at 100° for 10 minutes. The ester bond between a peptide and the 3' terminal ribose of tRNA should be hydrolyzed under the latter conditions. Furthermore, a comparable slowly migrating polypeptide was not detected with the ribosome-bound forms of chloramphenicol acetyl transferase, ricin or dihydrofolate reductase. Thus, the slowly migrating polypeptide is uniquely related to rhodanese. The nature of the slowly migrating form has not been established but it is most likely that it is generated by translation through the UGA termination codon at the end of the rhodanese coding sequence resulting in translation of thirteen additional codons before termination occurs at an in-phase UAG codon. However, it is somewhat surprising that this longer precursor form is apparently quantatively converted to the soluble form during activation and release of the polypeptide.

Radioactively labeled methionine from CPM-SAc[$^{35}$S] Met-tRNA$_f$ added to the reaction mixture can only occur at the N-terminus of rhodanese, not internally. The thioester bond between CPM and the thiol of methionine acylated with mercaptoacetic acid is chemically and enzymatically stable under the incubation conditions used. CPM-SAcMet-tRNA is not deacylated by the methionyl-tRNA synthetase and tRNA$^{Met}_m$ cannot be enzymatically aminoacylated with CPM-SAc[$^{35}$S]methionine. Furthermore, a large excess of unlabeled methionine (350 µM) was included in the reaction mixture. This greatly reduced the specific radioactivity of any free [$^{35}$S]methionine that may be present and provides for incorporation of methionine into an internal position in the polypeptide. Thus, the molar amount of coumarin was taken to be directly proportional to the radioactivity from [$^{35}$S]methionine and radioactivity was used to normalize fluorescence intensity and spectral data so that the values given below for these parameters are directly proportional to the fluorescence quantum yield and can be compared between different experiments.

EXAMPLE 6
Distribution of Newly Synthesized CPM-labeled Rhodanese

The distribution of newly synthesized CPM-labeled rhodanese into the soluble and ribosome fraction, respectively, was analyzed after centrifugal precipitation of the ribosomes through a layer of sucrose solution immediately following its synthesis. Table I shows that [$^{14}$C]leucine was incorporated into internal positions in rhodanese polypeptides whose N-terminus was not modified with coumarin. In this case, non-radioactive fMet-tRNA$_f$ was used to initiate protein synthesis. About half of these newly synthesized polypeptides (62% based on [$^{35}$S]methionine and 43% based on [$^{14}$C] leucine) were found in the ribosome fraction. Most of the remaining newly formed protein was recovered in the supernatant. The protein product in the supernatant fraction was entirely full-length rhodanese, as judged by autoradiography of the dried polyacrylamide gel on which the polypeptides were analyzed (FIG. 1).

The molar amount of rhodanese synthesized in the cell-free transcription/translation system was determined from the incorporation of either [$^{35}$S]methionine or [$^{14}$C]leucine into rhodanese polypeptides. Under the conditions described, only one coding sequence was transcribed from the plasmid (pSP65), namely the mRNA for rhodanese. Incorporation of [$^{14}$C]leucine into peptides in reaction mixture lacking the plasmid was less than 5% of the incorporation in the presence of the plasmid and was subtracted as a blank. Full-length rhodanese contains 24 leucine residues per chain and has a molecular weight of 33,000. Thus, with knowledge of the percentage of full length product (nearly 100% for the supernatant fraction), the molar amount of full-length protein that was synthesized can be calculated from the N-terminal methionine or internal leucine that was incorporated. This value was used to calculate the specific enzymatic activity, units/mg of rhodanese. The units of rhodanese activity were determined as a mole of thiocyanate formed per minute.

EXAMPLE 7
Rhodanese Activity

Rhodanese in the supernatant fraction was enzymatically active with a specific enzymatic activity of 744 units/mg rhodanese based on incorporated [$^{14}$C]leucine. This activity is similar to the reported specific activity of native bovine rhodanese and to values determined using native rhodanese isolated from bovine liver. Thus, nearly all of the translation product released from the ribosomes into the supernatant fraction was folded into the native conformation. In contrast, the nascent polypeptides on the ribosomes have no enzymatic activity. A similar situation exists when coumarin-[$^{35}$S]methionine forms the N-terminus of newly synthesized rhodanese: rhodanese in the supernatant is active whereas the polypeptides on the ribosomes are not enzymatically active.

Less [35S]methionine-labeled rhodanese was released from the ribosomes during the course of protein synthesis with the N-terminal probe but its apparent specific enzymatic activity (833 units/mg of rhodanese) was about 17% higher than the native enzyme. This appears to be due to removal of some of the N-terminal [$^{35}$S]methionine from newly formed enzyme.

EXAMPLE 8
Stability of Newly Synthesized Rhodanese

The stability of CPM-[$^{35}$S]methionine at the N-terminus of newly synthesized rhodanese was tested directly in the supernatant and ribosome fraction, respectively. About a 10% loss of trichloroacetic acid-precipitable radioactivity was observed over a 60-minute incubation at 37° C. with no loss of enzymatic activity in the supernatant fraction (data not shown). Native rhodanese lacks N-terminal methionine. Specific enzymes that remove methionine from the N-terminus of many proteins are known. In the case of in vitro synthesized rhodanese, polypeptides lacking the N-terminal coumarin-[$^{35}$S]methionine were not detected by radioactivity with the result that the amount of rhodanese protein present in these samples was underestimated. The higher specific enzymatic activity of the supernatant fraction calculated from N-terminal methionine (833 units/mg vs. 744 units/mg based on internal leucine, Table I) appears to reflect this underestimation of the rhodanese protein present in the samples. Also, a small portion of the rhodanese molecules may have been initiated with unlabeled endogenous formylmethionine from fMet-tRNA that was not eliminated during preparation of the S30 fraction. It should be noted that immediately after synthesis and centrifugation, the supernatant was treated with ribonuclease, then chromatographed on Sephadex G100 to separate CPM-labeled rhodanese from low molecular weight fluorescent compounds. In any event, Table I indicates that coumarin can be incorporated at the N-terminus of rhodanese and that these molecules are enzymatically active when released from the ribosomes.

TABLE I

Synthesis Of Enzymatically Active Rhodanese With N-Terminal CPM-SAcMet

| | Total Reaction Mixture Supernatant | Ribosomal | Fraction |
|---|---|---|---|
| N-term. CPM | | | |
| [$^{35}$S]- met Incorp. (pmol) | 3.4 | 2.1 | 1.2 |
| Enzyme Activity (units × 10$^{-3}$) | 32.1 | 0.0 | 33 |
| Specific Activity (units/mg) | 1 | 0.0 | 833[3] |
| Internal [$^{14}$C]leu | | | |
| Leucine Incorp. (pmol) | 65(2.7)[2] | 30 | 0 |
| Enzyme Activity (units × 10$^{-3}$) | 28(1.2)[2] | 0.0 | 0.0 |
| Specific Activity (units/mg) | 30.3(1.3)[2] | 31.0 | 744 |

Rhodanese was synthesized by coupled transcription/translation with CPM-SAc[$^{35}$S]Met-tRNA as the initiator tRNA or with fMet-tRNA$_f$ as the initiator tRNA and [$^{14}$C] leucine as the radioactive label. After 30 minute incubation at 37° C., the reaction mixture was centrifuged to obtain the ribosomal fraction and supernatant which were analyzed separately for amount of protein synthesized and enzymatic activity. Amounts are given for a 30 μl reaction mixture. The specific enzymatic activity of native rhodanese is about 750 units/mg protein. [1]Not calculated because of incomplete and full-length inactive rhodanese polypeptides on ribosomes. [2]Calculated pmol of enzyme in brackets (24 leucine residues/rhodanese polypeptide). [3]This apparent specific enzymatic activity is consistently found to be greater than the specific activity of native rhodanese.

EXAMPLE 9

Fluorescence Characteristics of CPM-labeled Rhodanese

The fluorescence parameters of CPM-SAcMet-rhodanese either free in the supernatant or bound to ribosomes are summarized in Table II. The corresponding emission spectra are given in FIGS. 3A and 3B. For comparison, data are included in Table II for CPM-SAc-Met-tRNA$_f$ free in solution or bound to ribosomes. The molar amount of N-terminally labeled CPM-SAcfMet-tRNA$_f$ or rhodanese (based on [$^{35}$S]methionine) was similar in each sample; then the fluorescence data were normalized by radioactivity to a common molar amount of coumarin. The fluorescence quantum yield, Q, is given relative to the quantum yield of enzymatically active CPM-SAcMet-rhodanese in the supernatant fraction, for which a relative quantum yield of 1.00 was assigned (Table II). Thus the spectra and relative quantum yield values presented in different figures and tables herein can be compared directly.

The quantum yield of the enzymatically active CPM-rhodanese in the supernatant fraction was somewhat higher than CPM-rhodanese bound to ribosomes (relative quantum yield of 1.00 vs. 0.89), but both were considerably higher than fluorescence from CPM-SAcMet-tRNA$_f$, either free in solution (Q=0.43) or bound into the peptidyl transferase center of ribosomes (Q=0.63). The latter was the situation before peptide synthesis was initiated to form nascent rhodanese with CPM-SAcmethionine at its N-terminus. The quantum yield reflects the local environment of the coumarin probe. For free coumarin or CPM-cysteine, the quantum yield increases with a bathochromic shift in the emission spectrum with solvents of decreasing polarity. For comparison, the absolute quantum yield and the emission maximum for free CPM-cysteine are 0.31 and 486 nm, respectively, in water, but these values are 0.91 and 470 nm in 95% ethanol, 0.51 and 460 nm in dioxane. Thus, the spectral data of Table II appear to indicate that the coumarin probe of CPM-SAcMet-tRNA$_f$ bound to ribosomes encounters a more hydrophobic environment when it is present at the N-terminus of a nascent peptide, but still held as peptidyl-tRNA on the ribosomes. There was a further increase in quantum yield as the nascent rhodanese was released in enzymatically active form into the supernatant fraction. These differences appear to reflect different stages in folding of the nascent rhodanese eventually into native conformation as considered further below. Fluorescence anisotropy was about 0.17 for CPM-Met-tRNA$_f$ free in solution and about 0.36 when bound to ribosomes (Table II). Anisotropy for CPM-Met at the N-terminus of ribosome-bound rhodanese was 0.31, but dropped to 0.18 when the enzyme was released from the ribosomes in enzymatically active form into the supernatant. This difference appears to reflect constraint of the movement of the fluorophore that is caused by the ribosome due to steric hindrance of the movement of the probe itself and/or the difference in the rotational relaxation or tumbling time in solution of free rhodanese and ribosome-bound rhodanese, respectively. The latter parameter reflects the difference in mass of rhodanese and ribosomes.

TABLE II

Fluorescence Characteristics of CPM-SAcMet-Rhodanese and CPM-SAcMet-tRNA free in solution and bound to ribosomes

| Fraction Analyzed | $E_{max}^1$ (nm) | Rel. Q[2] | A[3] |
|---|---|---|---|
| A. CPM-Rhodanese | | | |
| Supernatant | 473 | 1.00 | 0.18 |
| Ribosome-Bound | 471 | 0.89 | 0.31 |
| B. CPM-SAcMet-tRNA$_f$ | | | |
| Supernatant | 487 | 0.43 | 0.17 |
| Ribosome-Bound | 480 | 0.63 | 0.36 |

Fluorescence characteristics for rhodanese were determined with samples identical or similar to those used to determine synthesis and enzymatic activity of rhodanese given in Table I. Fluorescence data for CPM-SAcMet-tRNA (B. above) are included for comparison. [1]$E_{max}$: wavelength of emission maximum. [2]Rel. Q: relative fluorescence quantum yield; it was determined from the integrated fluorescence emission spectrum, normalized on the basis of [$^{35}$S] methionine radioactivity and expressed relative to the quantum yield of enzymatically active CPM-SAcMet-rhodanese (cf. Table I) in the supernatant fraction. [3]A: fluorescence anisotropy

EXAMPLE 10

Effect of Chaperones on Ribosome-bound CPM-rhodanese

The enzyme released from the ribosome in the presence of the chaperones was enzymatically active with a specific activity similar to that of native rhodanese, and contained a high proportion of enzyme molecules in the native conformation. In contrast, ribosome-bound rhodanese was enzymatically inactive.

The present invention illustrates the effects of the chaperones (DnaJ, DnaK, GrpE, GroEL, GroES) on fluorescence from ribosome-bound, enzymatically inactive nascent CPM-rhodanese and correlates effects observed with the release and specific enzymatic activity of the enzyme. The latter was taken as a measure of correct folding of rhodanese into its native conformation. Each of the five chaperones were added individually, then all together simultaneously to reaction mixture containing ribosomes with full-length rhodanese under non-translating conditions.

Table IIIA shows that the chaperones DnaK and GroES each cause a significant release of rhodanese polypeptides as reflected by a decrease in fluorescence anisotropy. In contrast, DnaJ caused a small but significant increase in anisotropy. The chaperones GrpE or GroEL had very little effect on fluorescence. A considerably larger effect, on both the amount of protein released from the ribosomes and fluorescence, was observed when the ribosomes were incubated with all of the chaperones together. The reaction mixtures were then separated by centrifugation into ribosome and supernatant fractions.

The amount in pmol of [$^{35}$S]methionine in rhodanese polypeptides in the supernatant fraction is given in Table IIIB. The specific enzymatic activity of rhodanese in the supernatant fraction after incubation with all chaperones together approached that of native rhodanese, 695 units/mg compared with 745 for the native enzyme. The quantum yield, anisotropy and emission maximum of the released material also were very similar to those for enzymatically active rhodanese (cf. Table II). In contrast, rhodanese released from the ribosomes in the presence of only DnaK or GroES was essentially enzymatically inactive even though it was composed of more than 90% of full-length rhodanese polypeptides (data not shown). Also, its quantum yield and emission maximum were different from those for enzymatically active rhodanese, suggesting that the material was not folded into the native conformation. Thus, the present invention demonstrates that chaperones promote efficient folding into the native conformation only when they function together on the ribosome-bound nascent rhodanese. DnaK or GroES cause some release of nascent chains from the ribosomes, but other chaperones are required to complete the folding process on the ribosomes.

TABLE III

Chaperone-mediated changes in fluorescence from CPM-SAcMet-rhodanese bound to ribosomes Additions to
A. Ribosomes with CPM-[$^{35}$]Met-labeled rhodanese

| (nm) | E max[1] | Rel Q[1] | A[1] |
|---|---|---|---|
| None | 471 | 0.89 | 0.31 |
| DnaJ | 471 | 0.92 | 0.32 |
| DnaK | 473 | 0.97 | 0.26 |
| GrpE | 471 | 0.89 | 0.29 |
| GroEL | 472 | 0.90 | 0.30 |
| GroES | 474 | 0.94 | 0.25 |
| All together | 475 | 1.03 | 0.21 |

B. Supernatant fraction from A above

| | E max[1] (nm) | Rel Q[1] | A[1] | Rhodanese released (pmol) | Specific Enzyme activity (units/mg) |
|---|---|---|---|---|---|
| None | * | * | * | 0.22 | |
| DnaJ | * | * | * | 0.15 | |
| DnaK | 485 | 1.17 | 0.19 | 1.95 | 2 |
| GrpE | * | * | * | 0.22 | |
| GroEL | * | * | * | 0.30 | |
| GroES | 480 | 1.12 | 0.19 | 1.50 | 3 |
| All together | 473 | 1.00 | 0.18 | 2.61 | 695 |

Ribosomes containing 4.5 pmol of CPM-SAc[$^{35}$S] methionine in nascent rhodanese peptides were incubated for 10 minutes at 37° C. under nontranslating conditions with the indicated chaperones. The fluorescence characteristics of the reaction mixtures were either determined directly (Part A) or for the supernatant fraction only after centrifugation (Part B). Enzymatic activity was determined only for the supernatant fraction. [1]Abbreviations as explained in Table II. * inadequate material to reliably measure fluorescence.

The quality of the commercial chaperones was assessed by SDS-PAGE followed by Coomassie staining. The chaperones gave a single band of the expected size or eletrophoretic mobility except GroES which contained some higher molecular weight contaminations and DnaJ which was visible as a doublet. All chaperones used were examined for contaminations by release factor 1 or release factor 2. Western blots from SDS-polyacrylamide gels were probed with the respective antibodies. Neither release factor was detected in any of the chaperone preparations by this procedure (data not shown).

Table III shows that no single chaperone was able to convert inactive ribosome-bound rhodanese into the native conformation. Next, sequential addition of one or two chaperones was examined. An unanticipated aspect of the present invention illustrated in Table IV was that the order of addition appears to be important. Enzymatically active rhodanese was obtained only when DnaJ was added first followed by DnaK and GrpE and finally GroEL plus GroES (Section A of Table IV). Release and activation were associated with a decline in anisotropy and an increase in the relative quantum yield. In contrast, anisotropy remained high and the quantum yield changed very little when GroEL/ES were the first chaperones with which the ribosome-bound rhodanese polypeptides were incubated followed by the missing chaperones (Section B in Table IV). Enzymatic activity was near the lower limit of detection in this situation. In Table IV, the fluorescence parameters were determined in the whole reaction mixture, whereas enzymatic activity was determined in the supernatant fraction after centrifugation. GroEL/ES may affect the fluorescent rhodanese molecules still bound to the ribosomes or those released before GroEL/ES were added.

TABLE IV

The effect of sequential addition of the chaperones

| Sequential Additions | E max[1] (nm) | *Rel Q[1] | A[1] | Spec. Enzym. Act.[2] (units/mg rhod.) |
|---|---|---|---|---|
| A. | | | | |
| None (↓+) | 471 | 0.89 | 0.31 | 0 |
| DnaJ (↓ then +) | 471 | 0.92 | 0.33 | 0 |
| DnaK + GrpE (↓ then +) | 474 | 1.01 | 0.26 | 2 |
| GroEL + GroES | 480 | 1.20 | 0.20 | 217 |
| B. | | | | |
| None (↓+) | 471 | 0.89 | 0.31 | 0 |
| GroEL + GroES (↓then +) | 473 | 0.91 | 0.29 | 3 |
| GrpE (↓ then +) | 473 | 0.91 | 0.29 | 3 |
| DnaK + DnaJ | 474 | 0.93 | 0.27 | 9 |

Ribosomes containing 4.5 pmol of CPM-SAc[$^{35}$S] methionine of nascent rhodanese polypeptides were incubated for 10 minutes each at 37° C. with the indicated chaperones in the order given under A or B. Fluorescence parameters were determined as before, then the samples were centrifuged and the resulting supernatant analyzed for amount of rhodanese released and its enzymatic activity from which specific enzymatic activity was calculated. [1]Abbreviations as explained in Table II. [2]Measured in the supernatant. After incubation under the given conditions and fluorescence measurements, the ribosomes were separated from the supernatant as described above.

EXAMPLE 11

Requirements For Enzymatically Inactive Rhodanese Conversion

The present invention also shows the chaperone and incubation requirements for the conversion of enzymatically inactive rhodanese to an enzymatically active conformation. The work shown in Table IV, section A, was repeated through the point at which DnaK/GrpE were added (before the addition of GroEL+GroES), then the sample was centrifuged to quickly separate the released protein from the ribosome-bound rhodanese peptides. The supernatant containing released full-length rhodanese peptides was pipetted back into the fluorescence cuvette, the fluorescence parameters were determined (Table V, section A, line 1) and GroES/EL was added (line 2). After a 10 minute incubation, the spectrum was retaken and anisotropy calculated as before. Similarly, the ribosome fraction containing ribosome-bound rhodanese was analyzed after it had been resuspended in Solution B, and re-incubated in the absence or presence of GroES/EL. Then the spectral properties of the samples were determined (Table VB, first 2 columns). Finally, the samples were centrifuged again to yield a supernatant and ribosome fraction. The amount and specific enzymatic activity were determined for the released rhodanese that was present in this supernatant fraction (Table VB, last 2 columns). Table V shows that about 1.8 pmol of CPM-rhodanese was released (about 30% of the ribosome-bound CPM-rhodanese in the original sample) into the supernatant after incubation with DnaJ, DnaK and GrpE but without the addition of GroEL/ES. This material had low anisotropy (as expected) and no enzymatic activity. Addition of GroEL/ES to this fraction containing released CPM-rhodanese had no effect on anisotropy and only a minimal effect on enzymatic activity. CPM-rhodanese associated with ribosomes had a very high anisotropy before GroEL/ES addition in that CPM-rhodanese that had been released by DnaK during the preceding incubation had been eliminated from the sample by centrifugation. Anisotropy dropped sharply upon addition of GroEL/ES (Table VB) and enzymatic activity was detected. The specific enzymatic activity of this released protein was that of the native enzyme.

Table V demonstrates that GroEL/ES have little or no effect on released rhodanese polypeptides but appear to bring about activation and release of ribosome-bound rhodanese following a previous, separate incubation of the ribosomes with DnaK, DnaJ and GrpE. For comparison, results are included in Table VC for rhodanese polypeptides released from the ribosomes by puromycin. None of the chaperones had a detectable effect on either the enzymatic activity or fluorescence from CPM-rhodanese after incubation of the ribosomes with puromycin. Similarly, none of the chaperones individually or combined had any effect on the enzymatic activity or fluorescence of enzymatically active CPM-rhodanese that was released from the ribosomes during the original coupled transcription/ translation (data not shown).

TABLE V

Effect of GroEL/ES on released and ribosome-bound rhodanese

|  | Rel. Q[1] | A[1] | amount (pmol) | Specific enzymatic activity (units/mg) |
|---|---|---|---|---|
| A. Released Rhodanese (Supernatant fraction) | | | | |
| none | 1.16 | 0.187 | 1.8 | 0 |
| GroEL/ES | 1.17 | 0.187 | 1.8 | 6.7 |
| B. Ribosome fraction | | | | |
| none | 0.83 | 0.373 | 0.1 | 0 |
| GroEL/ES | 0.98 | 0.221 | 1.4 | 728 |
| C. Rhodanese released with puromycin (supernatant fraction) | | | | |
| none | 1.21 | 0.199 | 2.2 | 0 |
| all chaperones | 1.20 | 0.198 | 2.1 | 0 |

For TABLE V, CPM-Met-rhodanese bound to ribosomes (about 4.5 pmol) was incubated in Solution B with DnaJ, DnaK and GrpE. Next, the sample was centrifuged and the supernatant and ribosome fraction were analyzed after the latter had been resuspended in the same volume of Solution B. Spectra were taken, amount and the activity of rhodanese was determined from a small aliquot. Then GroEL and GroES were added to each sample and the measurements repeated. With the ribosome fraction, after addition of GroEL/ES, the sample was centrifuged again in the airfuge and the amount and specific enzymatic activity of rhodanese was determined.

For Table V, part C, CPM-rhodanese bound to ribosomes was incubated for 10 minutes at 37° C. with 2 mM puromycin, then the incubation mixture was centrifuged. Only the resulting supernatant was analyzed after another incubation without or with chaperones. [1]The abbreviations are identified in Table II

EXAMPLE 12

Sparsomycin Blocks Release of Ribosome-bound CPM-rhodanese

The antibiotic sparsomycin binds to 50S ribosomal subunits with a $K_d$ of about 0.1 M and inhibits the peptidyl transferase reaction. In micromolar concentrations, sparsomycin had no effect on coumarin fluorescence from ribosomes bearing CPM-rhodanese. First, sparsomycin and then the chaperones were added individually as described in Table III. Table VI shows that none of the chaperones had any detectable effect on the fluorescence parameters measured. When the chaperones were added in groups (not shown) or individually after sparsomycin, there were only very small changes in anisotropy compared to the data given in Table IIIA indicating that most of the CPM-rhodanese polypeptides remained bound to the ribosomes. This was verified by centrifuging the sample after the fluorescence measurement were completed. Less than 10% of the rhodanese molecules were released into the supernatant in the presence of sparsomycin and this released material was enzymatically inactive (data not shown). Thus, sparsomycin prevents release of rhodanese by DnaK or GroES from the ribosomes. In that sparsomycin interferes with the peptidyl transferase reaction, the present invention demonstrates that CPM-rhodanese is held on the ribosomes as peptidyl-tRNA and that release by DnaK and/or GroES involves the peptidyl transferase center in a reaction by which the bond between the tRNA and the polypeptide is hydrolyzed.

TABLE VI

Sparsomycin prevents chaperone-mediated changes in fluorescence from CPM-SAcMet-rhodanese bound to ribosomes

| Additions | max[1] | Q[1] | A[1] |
|---|---|---|---|
| None | 471 | 0.89 | 0.31 |
| first sparsomycin then: | 471 | 0.90 | 0.30 |
| DnaJ | 471 | 0.90 | 0.31 |
| or DnaK | 471 | 0.92 | 0.30 |
| or GrpE | 471 | 0.90 | 0.30 |
| or GroEL | 471 | 0.90 | 0.30 |
| or GroES | 473 | 0.91 | 0.29 |
| DnaJ + DnaK | 471 | 0.92 | 0.32 |
| All together | 471 | 0.90 | 0.29 |

Experimental conditions were the same as in Table III except 4 μM sparsomycin was added before the addition of each of the chaperones individually. None of the chaperones caused release of more than a few percent CPM-rhodanese into the supernatant.

EXAMPLE 13

Accessibility of the N-terminal Coumarin to Nitromethane

Figure 2:
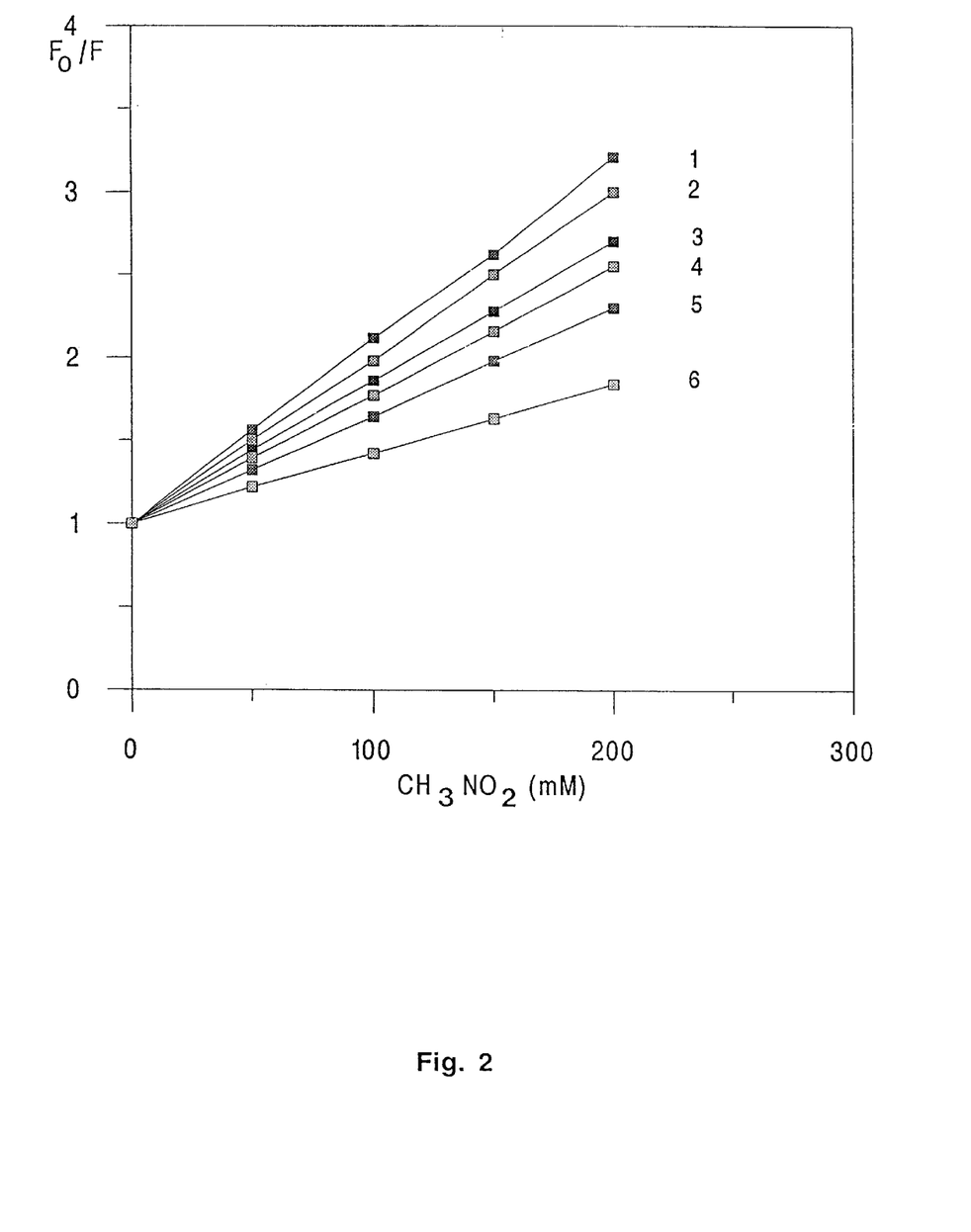

Quenching of fluorescence from CPM-rhodanese peptides by nitromethane was evaluated as a measure of the accessibility of the probe in different situations. Nitromethane is a water soluble, un-ionized small molecule that efficiently quenches coumarin fluorescence in solution by collision with the probe. Stern-Volmer plots are shown in FIG. 2. CPM-Met-tRNA$_f$ free in solution and bound to ribosomes exhibit the highest and lowest quenching, respectively. Free in solution, the fluorophore is relatively accessible whereas it is largely shielded from nitromethane, when the CPM-Met-tRNA$_f$ was bound to ribosomes. CPM at the N-terminus of enzymatically active rhodanese in solution also was relatively accessible. This is consistent with the anisotropy data for enzymatically active rhodanese (Table II) and the crystal structure of rhodanese in which the N-terminal segment is exposed. Interestingly, quenching was significantly lower for rhodanese that has been released from the ribosomes with either DnaK or puromycin. This material was enzymatically inactive as shown in Tables III and V. The values obtained with both were similar, but lower than observed for free, enzymatically active rhodanese. Thus, the present invention demonstrates that the N-terminus of this released material is less exposed than for native rhodanese and that this protein is not folded into its native conformation. The even lower quenching with ribosome-bound rhodanese may be due in part to shielding by the ribosomes especially of nascent short peptides as well as incomplete folding of the full-length polypeptides.

EXAMPLE 14
Intermediate States Detected by Anticoumarin IgG

Figure 3A:
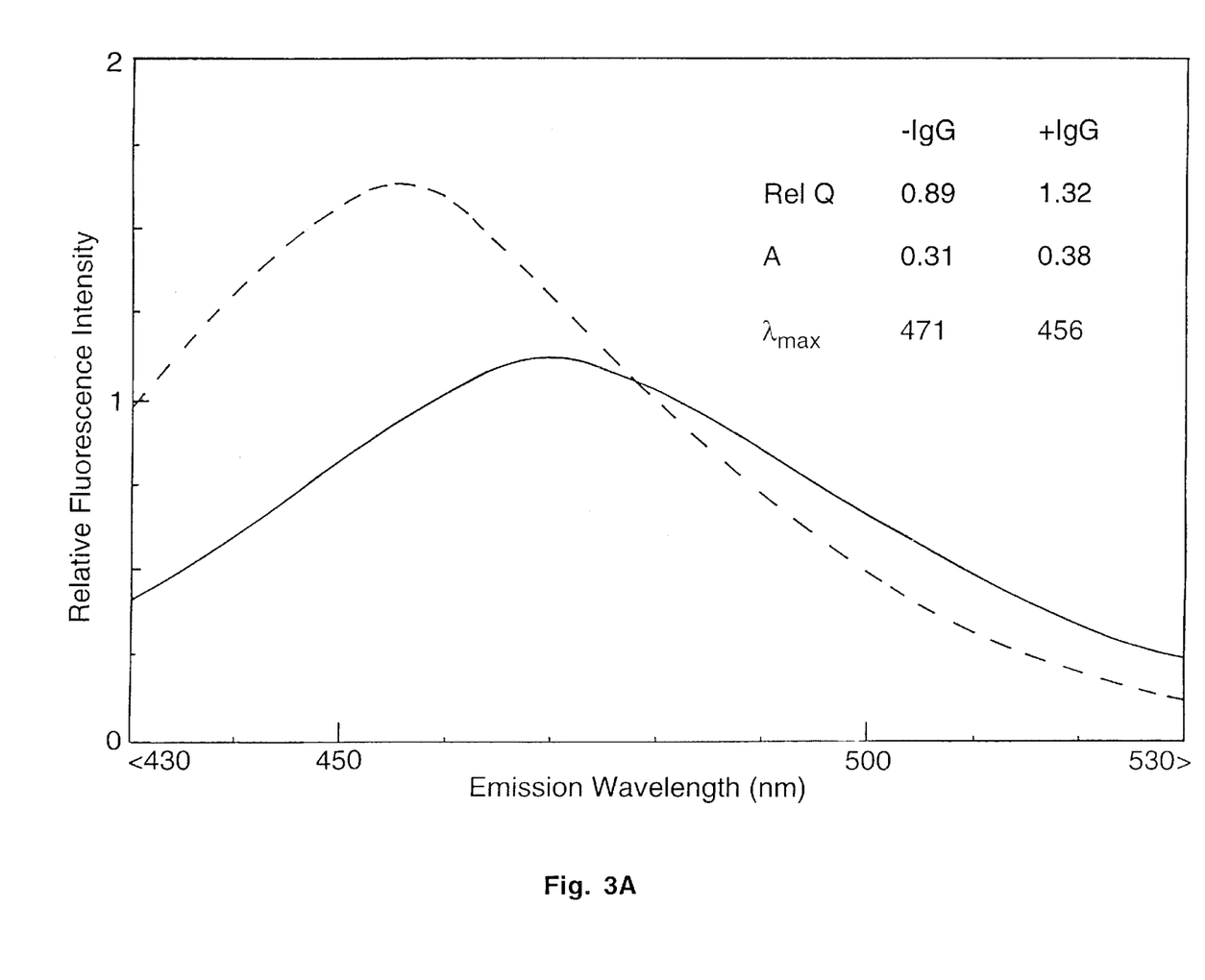
FIG. 3 shows the fluorescence emission spectra of CPM-labeled rhodanese before and after incubation with anti-coumarin antibodies. CPM-rhodanese bound to ribosomes (A) or released into the supernatant (B) were analyzed (solid line). Then anti-coumarin IgG was added and the spectra retaken (dashed line). The insert gives quantitative fluorescence data for the respective samples analyzed.
Figure 3B:
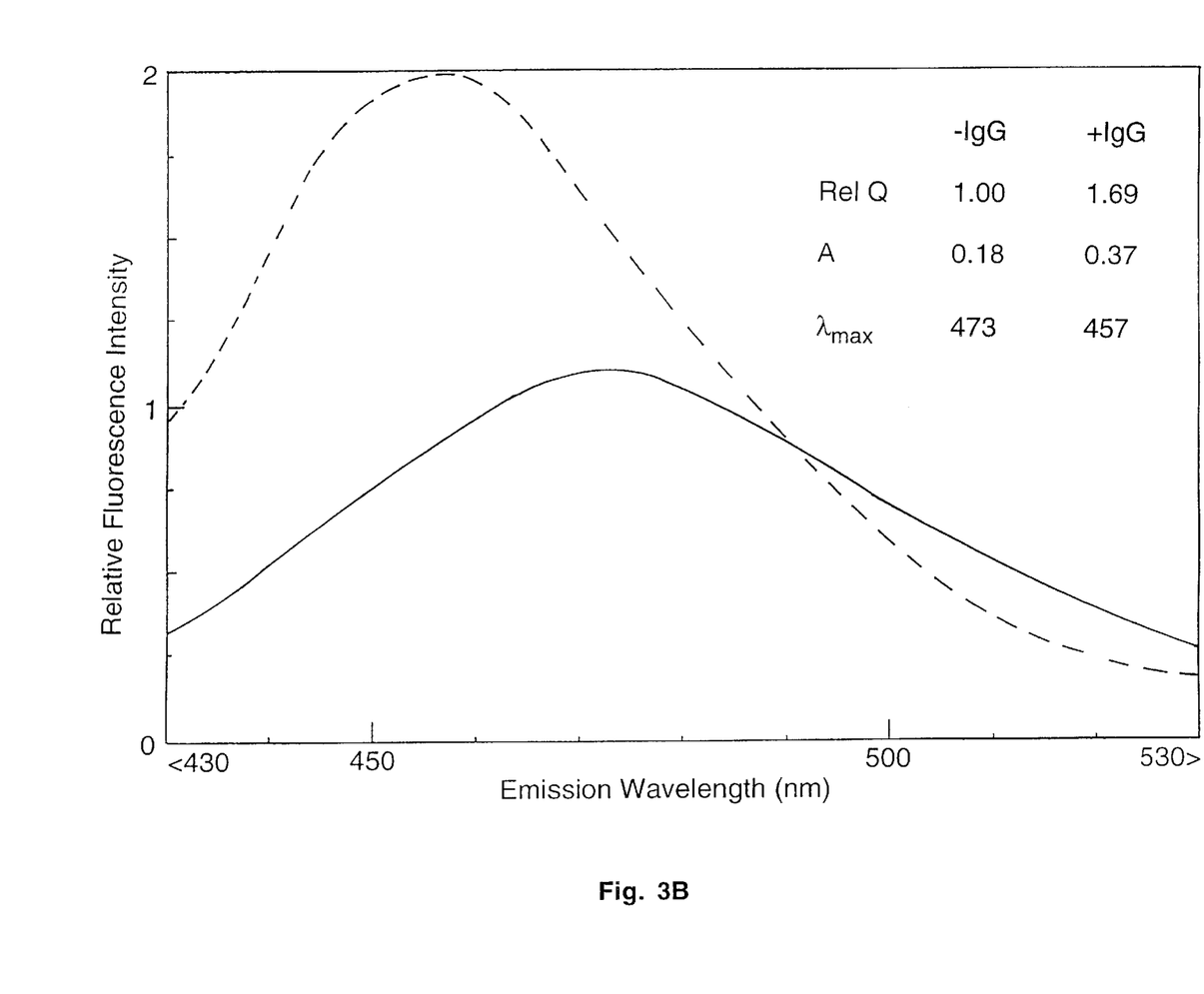

Polyclonal antibodies with high binding specificity for the CPM-fluorophore were used to evaluate folding of full-length rhodanese chains bound to ribosomes in comparison with enzymatically active rhodanese free in solution. FIGS. 3A and 3B indicate that the probe was accessible to the anticoumarin antibodies on both ribosome-bound and free CPM-rhodanese. For the latter, enzymatically active rhodanese was released from the ribosomes by incubation with all of the chaperones, then the ribosomes were removed from the reaction mixture by centrifugation as described in relation to Table II. The antibodies cause an increase in anisotropy and quantum yield that was associated with a bathochromic shift in fluorescence from both free and ribosome-bound CPM-rhodanese. In the presence of anti-coumarin IgG, the emission maximum, about 456 nm, was the same in both cases. The change in the quantum yield and emission maximum apparently reflects the increase in hydrophobicity of the environment of the probe that was caused by binding to the immunoglobulin. The increase in quantum yield caused by the antibodies was less with ribosome-bound rhodanese (FIG. 3A) than for enzymatically active CPM-rhodanese that was free in solution (FIG. 3B). This difference in quantum yield probably was due to partial shielding of shorter nascent peptides from the antibody by the ribosome. This phenomenon has been observed previously with both nascent polyalanine and nascent MS2 coat protein. Like previous results with CPM-SAcAla-tRNA, CPM-S Ac Met-tRNA$_f$ bound into the ribosomal P site, appears to be completely shielded from IgG in that there is no change in any of the three parameters upon incubation with anti-CPM IgG (data not shown).

Figure 4:
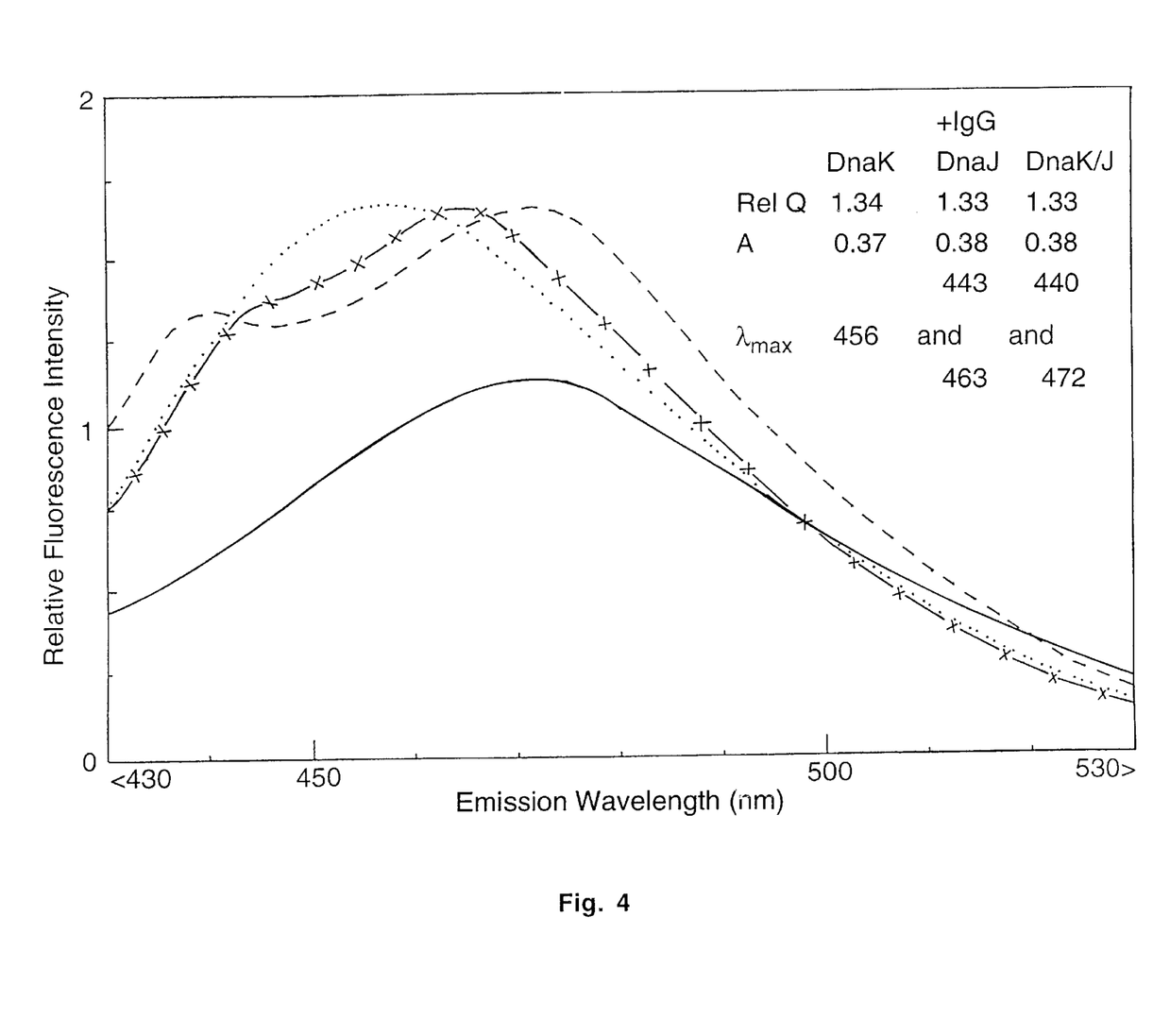

To demonstrate the effect of chaperones on ribosome-bound nascent CPM-rhodanese, first sparsomycin, then DnaJ or DnaK, individually or together were added to a reaction mixture containing ribosotnes similar to those used for FIG. 3A. In the presence of sparsomycin, very little rhodanese is released from the ribosomes, as discussed in relation to Table VI. After incubation, anti-coumarin IgG was added. The emission spectra from the resulting mixtures are shown in FIG. 4. The emission spectrum of a sample incubated with only sparsomycin (no chaperones or anti-coumarin IgG added) is given for comparison. GroEL and GroES separately or together did not cause any spectral changes like those seen with DnaJ without or with DnaK in the presence of IgG.

The spectra for the samples containing DnaK or DnaJ or both can be compared directly with the spectra of FIG. 3A which is from a sample containing ribosome-bound CPM-rhodanese with or without IgG in the absence of chaperones. Incubation with DnaK followed by IgG has little effect on the resulting emission spectrum, but a distinctly bimodal curve was apparent from the sample that was incubated with DnaJ. This effect was more pronounced for the sample containing both DnaK and DnaJ. In this case, distinct maxima occur in the spectrum at 435 nm and 472 nm. The latter is very near the maximum for free or ribosome-bound rhodanese in the absence of IgG as indicated in FIG. 3A and 3B.

The bimodal emission spectra indicate that in the presence of IgG, two fluorescent species were present in the samples that were incubated with DnaJ or DnaJ and DnaK. One possibility is that the anti-coumarin antibodies were able to interact with only part of the CPM-rhodanese because DnaJ was bound to the N-terminus of some nascent rhodanese peptides. Hartl and his coworkers presented data indicating that DnaJ can be chemically cross-linked to ribosome-bound nascent polypeptides. However, several lines of evidence suggest that DnaJ does not bind to the N-terminus of the ribosome-bound rhodanese—at least not in a way that detectably affects the N-terminal coumarin. First, DnaJ has no apparent effect by itself on quantum yield, anisotropy or emission maximum as shown in Table III. Second, DnaJ does not appear to shield the N-terminal coumarin. Shielding of some portion of the nascent CPM-rhodanese from IgG would result in a decrease in quantum yield and anisotropy compared to the sample without DnaJ. No such decrease is evident (compare insert of FIG. 4 with the insert of FIG. 3A). That IgG is bound to coumarin of both fluorescent species (max of about 440 nm and 470 nm, FIG. 4) is indicated by the similar change in fluorescence intensity that was caused by IgG in both of the regions of the emission spectra. Thus, FIG. 4 indicates that DnaJ causes a change in the state of either the nascent peptide or the ribosome that affects the nascent peptide in a way that affects the environment of the probe when it is bound to IgG. DnaK appears to facilitate this change that is caused by DnaJ.

EXAMPLE 15

In another application of the present invention, the yeast TATA box binding protein was synthesized in an *E. coli* S30 extract by coupled transcription/translation from a plasmid containing the coding sequence under the T7 promoter. In this case, T7 RNA polymerase was included in the incubation. The initiator tRNA was CPM-SAc [$^{35}$S]Met-tRNA$_f$.

In a 10 µl reaction mixture, about 125 ng N(coumarin) yeast TATA box binding protein was synthesized. The reaction mixture was enlarged 62 fold. After incubation, 600 µl of the reaction mixture containing about 7.5 µg of the labeled protein was loaded on a 0.5 ml column containing DEAE cellulose which had been equilibrated in 20 mM Tris-HCl, pH 7.9, 100 mM KCl, 0.5 mM ethylene diamine tetracetic acid (EDTA), 5 mM β-mercaptoethanol, and 20% glycerol (buffer A). About 0.75 µg of yeast TATA box binding protein did not absorb to the matrix, about 1.5 µg of N(coumarin)yeast TATA box binding protein was recovered by elution with 200 mM KCl in the same buffer solution. An additional 3.0 µg of the coumarin-labeled protein was recovered by elution of the column by 350 mM KCl. This material was loaded onto a heparin-Sepharose column (I ml bed volume) equilibrated in buffer A. Approximately half of the radioactively labeled protein absorbed and was eluted by increasing the salt concentration to 0.7 M KCl in buffer A.

The eluted protein was used to study by fluorescence the binding of yeast TATA box binding protein to specific DNA sequences. A mutated DNA sequence was used as a control. Changes in the quantum yield of coumarin fluorescence and fluorescence anisotropy indicate that the in vitro synthesized protein purified as described, specifically interacts with the DNA containing the TATA box.

With the cell-free translation system disclosed herein, protein synthesis proceeds at a relatively high linear rate for about 20 minutes before the rate declines rapidly. Enzymatically active rhodanese is formed and released from the ribosomes during the period of linear synthesis but failure of the system is associated with an accumulation of apparently full-length rhodanese polypeptides as peptidyl-tRNA in the peptidyl transferase center of the ribosomes. That these accumulated nascent polypeptides exist as peptidyl-tRNA in the ribosomal P site is indicated by their reactivity with puromycin and the effect of sparsomycin in blocking subsequent termination and release of the protein. As used herein, "termination" refers to only those reactions that are directly related to hydrolysis of the ester bond between the nascent polypeptide and tRNA, whereas "release" as used herein refers to the separation of the protein from the ribosome. The accumulated ribosome-bound nascent rhodanese was enzymatically inactive but was released and converted into fully active enzyme only by incubation of the ribosomes simultaneously with the five chaperones, DnaK, DnaJ, GrpE, GroEL and GroES. There was no detectable incorporation of amino acids into the nascent protein during this incubation under the conditions used. Rhodanese with reduced enzymatic activity was produced by incubating the ribosomes first with DnaJ, DnaK and GrpE followed by a second incubation of the ribosomes with GroEL and GroES. This appears to establish the order of these reactions and is supported by the results with DnaJ.

Protein released from the ribosomes by reaction with puromycin or by incubation with DnaK or GroES only was enzymatically inactive. This released protein was not activated by incubation with any combination of chaperones. This was somewhat surprising bacause GroEL and GroES efficiently promoted refolding into enzymatically active protein of rhodanese that had been denatured with urea or guanidine •HCl. Whether or not GroEL and GroES mediate folding on the ribosome itself or function with newly released protein before it undergoes secondary reactions that block the effect of GroEL and GroES remains to be established.

Changes in fluorescence from coumarin at the N-terminus of nascent rhodanese reflect the chaperone-dependent reactions that occur during activation, termination and release of the enzyme from the ribosome. Fluorescence from coumarin is very sensitive to the local environment of the fluorophore so that changes in the position of the probe in the ribosome, folding of the nascent peptide to which it is linked, or binding of a chaperone near the probe are likely to be reflected by changes in fluorescence quantum yield, emission maxima and anisotropy. Differences in these parameters for fully enzymatically active CPM-rhodanese that was released from the ribosomes and ribosome-bound CPM-rhodanese were evident and appear to reflect differences in the conformation of the protein. For instance, compare the relative quantum yield of enzymatically active, soluble CPM-rhodanese (Table II) with enzymatically inactive soluble rhodanese that has been released from the ribosomes by incubation with DnaK or GroES (Table III). It is unclear why these two apparently unrelated proteins with ATP promote release of the rhodanese. Their activity in this regard is reminiscent of the activity of release factor 3, RF-3, which has GTPase activity.

That rhodanese exists in different conformations is supported by FIG. 2 which illustrates differences in nitromethane quenching for the protein in different states. These differences are likely to reflect differences in shielding of the probe by the protein itself in different conformations. However, a striking feature is that none of the chaperones either individually or in combination cause a pronounced change in fluorescence comparable to that observed with anti-coumarin IgG (FIG. 3A and 3B). This appears to indicate that none of the chaperones interact directly with the N-terminus of the CPM-rhodanese. FIG. 4 shows that DnaJ promotes a reaction that affects the ribosome-bound nascent rhodanese as is evident from the results with anti-coumarin IgG. Following reaction with DnaJ, the N-terminal coumarin exists in two different states that can be distinguished by the anticoumarin antibody. The component with an emission maximum near 440 nm is produced by DnaJ alone but is intensified in the presence of DnaK, suggesting that the latter facilitates the reaction promoted by DnaJ. It is possible that these results reflect nascent chains of different length, e.g., one species or class that interacts with DnaJ or DnaK or both, whereas the other, presumably shorter form might not react with these chaperones. These two (hypothetical) different length classes probably represent different folding intermediates which occur as the nascent peptide is extended. The prominent effect seen in FIG. 4 was observed only in the presence of sparsomycin. Thus, the fluorescence species with maxima near 440 and 470 nm reflect intermediate states generated by DnaJ and DnaK that were trapped by sparsomycin. It follows that they must precede codon-directed hydrolysis of peptidyl-tRNA in the termination reaction sequence. The chaperones used were highly purified and appear to be free of release factors. A high proportion of release factors 1 and 2 were associated with ribosomes in *E. coli* cells.

It is not clear how or why chaperone-mediated reactions affect factor-mediated hydrolysis of the peptide-tRNA bond, termination, and release of the nascent protein from the ribosome. The former reaction was blocked by sparsomycin and is thought to involve the peptidyl transferase reaction. What may be a similar effect has been noted with proteins that are formed on the endoplasmic reticulum. The association of the signal recognition particle with the ribosome inhibits elongation of the nascent peptide until the signal recognition particle•nascent protein•ribosome complex interacts with the receptor or docking protein on the membrane of the endoplasmic reticulum.

There is a question of where in the ribosome the reactions of termination, folding and release take place. During polypeptide synthesis, aminoacyl-tRNA and short peptides as peptidyl-tRNA are held rigidly in a hydrophobic site, the peptidyl-transferase center, which is located at the base of the central protuberance of the large ribosomal subunit. The tRNAs are bound to specific sites on the interfacing surfaces between the two ribosomal subunits with the nascent peptide as peptidyl-tRNA positioned in the peptidyl transferase center. However, electron micrographs show that the exit domain, the region at which the nascent protein emerges from the ribosome, is located on the distal surface of the large subunit at a distance of up to 90 Å or more away from the peptidyl transferase center. The length of nascent polyalanine peptide in alanine residues was used to estimate the distance from the peptidyl transferase center to the point at which an N-terminal probe of the peptide became accessible to IgG or its Fab fragments, about 60 residues or 90 Å (1.5

Å/amino acid residue in the helical conformation) for the former and 40 residues or 60 Å for Fab. Anticoumarin Fab can react with peptides of shorter average length than the corresponding IgG from which it was derived, suggesting that its smaller size allows it to penetrate further into the ribosome. Chemical crosslinking of DnaJ to nascent peptide of chloramphenicol acetyl transferase and firefly luciferase as short as 55 amino acids in length on wheat germ ribosomes has been reported. This peptide length is in reasonable agreement with the results for polyalanine indicated above.

The present invention shows that the amino terminus of short, nascent peptides is shielded within a domain of the ribosome until they are extended to the length at which their N-terminus is well removed from the region of the peptidyl transferase center. This domain may involve the tunnel through the large ribosomal subunit as originally reported by Yonath and coworkers. Eisenstein et al. (1994) reviewed ribosome structural data indicating that one or more tunnels or cavities exist within the large ribosomal subunits between the peptidyl transferase center and the exit domain. Crowley and coworkers (1993) presented data indicating that the signal sequence of nascent eukaryotic membrane proteins moves through a similar tunnel during their synthesis. The present invention suggests that this cavity within the large ribosomal subunit provides a sanctuary in which at least part of the folding process can take place in an environment in which the nascent protein is partially sheltered from proteases and other degenerative processes that occur in the cytoplasm of the cell.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of synthesizing a fluorescently labeled protein in a prokaryotic, cell-free protein synthesis system, wherein said fluorescent label is on the N-terminus of said protein comprising the steps of:

(a) incubating a sample of ribosomes obtained from a cell-free extract with plasmid DNA containing a coding sequence -for a protein of interest, said sample incubated in a coupled transcription/translation medium together with an aminoacyl tRNA having fluorescent label;

(b) partially purifying said fluorescently labeled protein by separating newly synthesized, fluorescently-labeled protein from other fluorescent components within said sample;

(c) measuring the amount of protein synthesized;

(d) determining fluorescence of newly synthesized protein; and (e) determining the biological activity of the newly synthesized protein.

2. The method of claim 1, wherein said aminoacyl tRNA is an initiator-aminoacyl-tRNA.

3. The method of claim 1, wherein said flurorescent label is covalently attached to the amino acid of an initiator aminoacyl-tRNA.

\* \* \* \* \*

UNITED STATES PATENT AND TRADEMARK OFFICE
CERTIFICATE OF CORRECTION

PATENT NO. : 6,448,033 B1  Page 1 of 1
DATED : September 10, 2002
INVENTOR(S) : Wieslaw Kudlicki, Gisela Kramer and Boyd Hardesty It is certified that error appears in the above-identified patent and that said Letters Patent is hereby corrected as shown below:

Column 2,
Line 33, please delete the period after "electrophoretic".

Column 5,
Line 67, please delete the space between "CPM-S" and Ac".

Column 7,
Line 30, "full length" should read -- full-length --.
Line 54, "35S" should read -- $35_S$ --.

Column 13,
Line 59, "fraction" should read -- fractions --.

Column 14,
Line 25, "measurement" should read -- measurements --.

Column 15,
Line 57, "ribosotnes" should read -- ribosomes --.

Column 17,
Line 40, "bacause" should read -- because --.

Column 20,
Line 19, please delete the hyphen before the word "for".

Signed and Sealed this

Twelfth Day of August, 2003

JAMES E. ROGAN
*Director of the United States Patent and Trademark Office*